United States Patent [19]

Pameijer

[11] 4,014,097

[45] Mar. 29, 1977

[54] METHOD AND APPARATUS FOR MEASURING AND RECORDING THREE-DIMENSIONAL CONDYLERMOVEMENTS OF THE MANDIBLE

[75] Inventor: Cornelis H. Pameijer, Wakefield, Mass.

[73] Assignee: Trustees of Boston University, Boston, Mass.

[22] Filed: Aug. 14, 1975

[21] Appl. No.: 604,785

[52] U.S. Cl. .................................................. 32/20
[51] Int. Cl.² ........................................ A61C 9/00
[58] Field of Search ................... 32/19, 20, 32, 21; 128/2 R, 2 S

[56] References Cited

UNITED STATES PATENTS

| | | | |
|---|---|---|---|
| 2,814,876 | 12/1957 | Stuart | 32/19 |
| 3,452,439 | 7/1969 | Lee | 32/32 |
| 3,614,950 | 10/1971 | Rabey | 32/20 X |

*Primary Examiner*—Robert Peshock
*Attorney, Agent, or Firm*—Munroe H. Hamilton

[57] ABSTRACT

A dentistry aid is comprised by a recording system which is concerned with occlusion and related movements of the condyles in the tempero mandibular joints of a patient. Condyle movement, occurring in working the jaws and teeth, is known to be a complicated three-dimensional movement. The recording system of the invention is employed to carry out a method of sensing changes in positional relationship of the condyles with reference to respective maxilla cavities, and determining and recording condyle movements in at least three dimensions. Data obtained by this method constitute a valuable adjunct to the dental profession, particularly in connection with occlusion adjustment.

Included in the recording system of the invention is a pair of cooperating frame structures comprising an upper stationary frame part attachable to the teeth of the upper jaw and a lower movable frame part attachable to the teeth of the lower jaw. Pressure sensing housing units, supported at the extremities of the stationary frame part, include sensing elements yieldably supported thereon. Pressure-transmitting actuator units are supported at the extremities of the lower frame structure in nested relationship with respect to the housing units. Contact elements, adjustably mounted in the actuator units, engage against respective sensing elements to selectively activate the sensing elements in response to three-dimensional condylar movements of the mandible. Gauging means connected to the sensing elements are operable to determine and record, either electrically or mechanically, the extent of condylar movements of the mandible when the jaws and teeth are worked.

4 Claims, 10 Drawing Figures

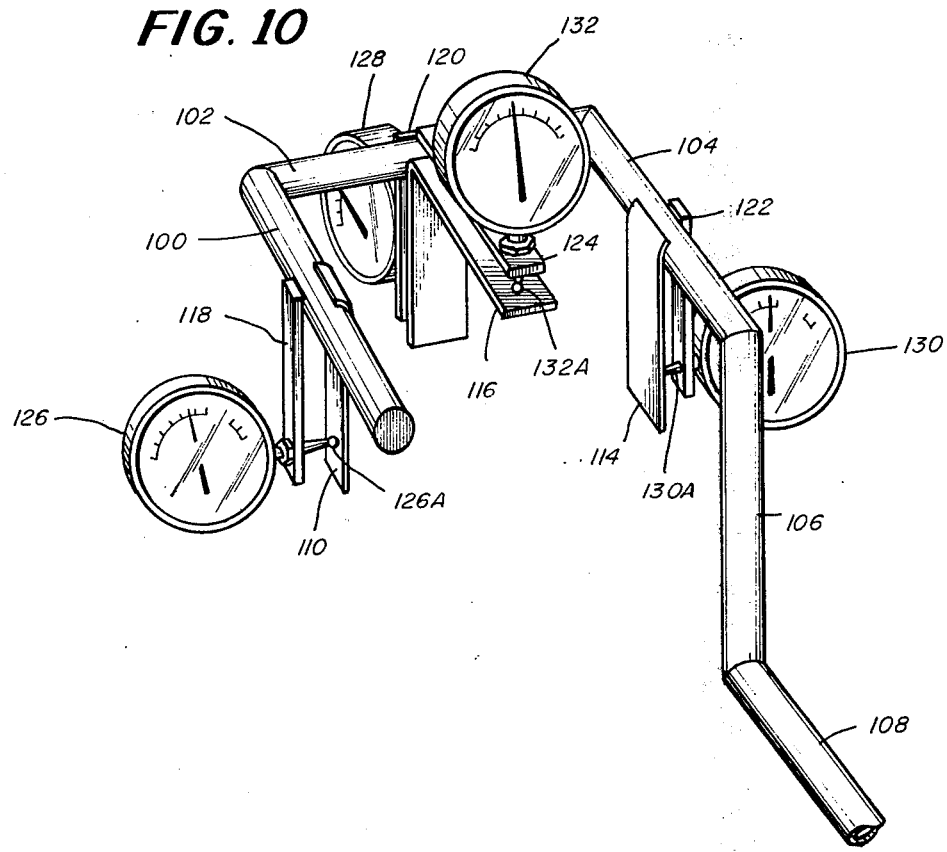

METHOD AND APPARATUS FOR MEASURING AND RECORDING THREE-DIMENSIONAL CONDYLERMOVEMENTS OF THE MANDIBLE

BACKGROUND OF THE INVENTION

In the dentistry profession, it is recognized that establishing proper occlusion for a patient is closely interrelated with condylar position of the mandible created by the tempero mandibular joint. Correct location of the condyles reflects the health and comfort of the patient. Not only the position of the joint, but movement as well, is complex and of extreme importance to the dentist. This is particularly so in the case of certain dental procedures.

For example, extensive restoration in natural teeth involves knowledge of the position of the condyles in the tempero mandibular joint. Secondly, patients suffering from tempero mandibular joint syndrome usually demonstrate hypomobility of one or both condyles. The recording of this hypomobility as a record which is an aid in diagnosing the syndrome and subsequent follow-up recordings after treatment will enable the dentist to establish the success of the therapy. Another possibility is the recording of pertinent data for each individual patient which then can be transferred to a dental articulator which will imitate these movements to a great degree of accuracy thus allowing a model of the patient which can be utilized in the laboratory.

Various methods for adjusting occlusion are presently in use involving clinical judgment and evaluation and utilization of factors such as tooth mobility, abnormal wear patterns, and X-ray findings of a widened periodontal ligament space. However it has been learned that in using these various accepted techniques to obtain a true centric relation wherein all teeth of both jaws meet normally with perfect distribution of forces throughout the dental arch, there may result differing relations indicating that additional unfavorable factors need to be taken into consideration. So far as is known, no presently disclosed systems in the art are capable of providing the desired information.

BRIEF DESCRIPTION OF THE INVENTION

The present invention is concerned with the field of dentistry and comprises a method and apparatus for assembling data constituting a valuable dentistry aid for dealing with restorations in natural teeth or treating patients suffering from tempero mandibular joint syndrome, and for preparing and fitting dentures. More particularly, the invention is concerned with a method and apparatus for sensing changes in positional relationship of the condyles with reference to respective maxilla cavities occurring in working the jaws and teeth of a patient. As these changes in positional relationship take place, condylar movements in at least three dimensions are determined and recorded.

It is, therefore, a chief object of the invention to provide data in recorded form dealing with postural position and compressibility of the mandibular joints whereby reproduceability and degree of distillization of the rounded mandible ends in three dimensions in any given instance may be more fully determined and utilized in carrying out various dentistry techniques.

As one satisfactory means of realizing the objective noted above, I have conceived of a method of yieldably supporting at opposite sides of the head of a patient, and in spaced relation thereto, a plurality of sensing elements and selectively displacing the sensing elements by pressure-responsive actuator elements in response to three-dimensional condylar travel of the mandible when the jaws and teeth are worked.

In carrying out this method of the invention, I have further devised a unique sensing and recording apparatus comprising a pair of cooperating frame structures including a stationary sensing frame structure attachable to the teeth of the upper jaw of a patient, and a movable actuator frame structure attachable to the teeth of the lower jaw and movable therewith. At the extremities of the stationary sensing frame structure are located a pair of pressure sensing housing units located at either side of the head of the patient. At the extremities of the movable lower frame structure are mounted a pair of pressure responsive units arranged in nested relationship within the pressure sensing housing units. In the pressure responsive actuator units are contact elements engageable with respective sensing elements in the pressure sensing housing units, and operable to selectively displace sensing elements of the pressure sensing housing units in response to movement of the condyles in the mandibular joint. The upper and lower frame structures are provided with clamping means for fastening these structures firmly against the teeth of respective upper and lower jaws. In one desirable form of the invention, displacement of sensing elements may be electrically recorded, and in another desirable form of the invention, displacement may be mechanically indicated.

The nature of the invention and its other objects and novel features will be more fully understood and appreciated from the following description of a preferred embodiment of the invention selected for purposes of illustration and shown in the accompanying drawings.

BRIEF DESCRIPTION OF THE DRAWINGS

FIG. 10 is a perspective view illustrating a modification of the invention.

DETAILED DESCRIPTION OF THE INVENTION

Figure 1:
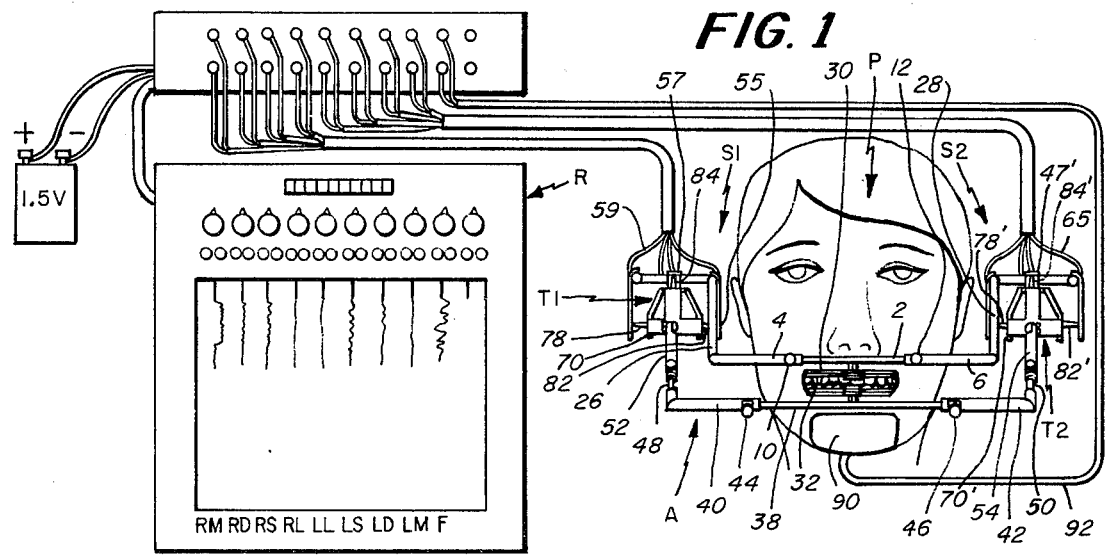
FIG. 1 is a diagrammatic view illustrating the apparatus of the invention in an operative position and showing schematically means for electrically recording condylar movements of the mandibular joint of a patient.
Figure 2:
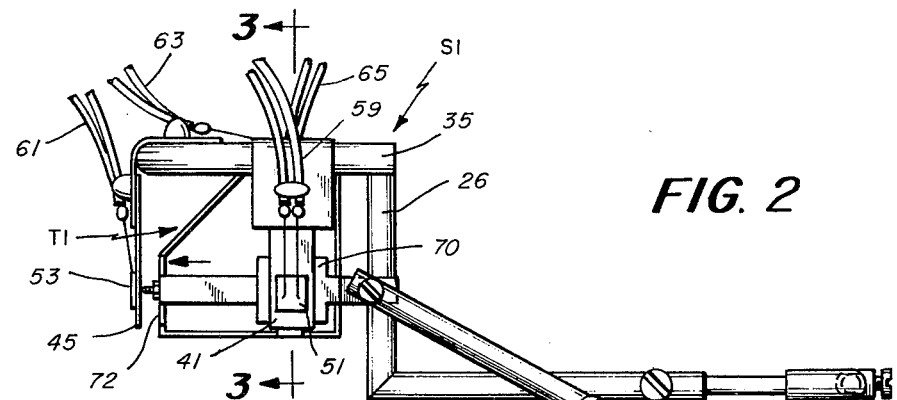
FIG. 2 is a side elevational view of pressure sensing and pressure responsive actuator means in the apparatus of the invention.

Referring more in detail to the drawings, FIG. 1 illustrates a patient denoted by arrow P and further showing the recording system of the invention carried to the teeth of the patient in a typical operating position to sense and record condylar movements of the mandible of the patient P. The recording system, as shown in FIG. 1, generally includes a stationary upper frame structure, a movable lower frame structure, and pressure recording means connected to pressure sensing components of the upper frame structure.

The upper frame structure is designed to be clamped to the maxillary teeth of patient P in the manner suggested in FIG. 1, and has supported at two extremities thereof a pair of pressure sensing housing units. Similarly, the lower frame structure is designed to be clamped to mandibular teeth and has at its extremities a pair of pressure transmitting actuator units which are arranged in nested relationship in the respective pressure sensitive housing units. The pressure sensing housing units and the nested pressure transmitting actuator units are, in accordance with the invention, further arranged in a specially oriented relationship with respect to the tempero mandibular joints at either side of the patient's head such that they lie in substantially centered relationship with respect to a horizontal hinging axis passing through these mandibular joints.

Considering these parts in greater detail, the upper stationary frame structure comprises a U-shaped retaining body which is adjustable in at least two dimensions and which is designed to be secured to the maxillary teeth of a patient, as shown in FIG. 1. This upper retaining body, when thus attached, presents a front section 2 extending transversely in front of the face of the patient P in spaced relationship thereto. Slidably disposed on the center section 2 are end sections 4 and 6 adapted to be detachably secured by means of set screws 10 and 12.

At their outer extremities, the end sections 4 and 6 are bent at right angles and have received therethrough the pair of side reactions denoted by numerals 14 and 16. These side sections are slidably received in side extensions 18 and 20, detachably secured by set screws 22 and 24. Extending upwardly from the extensions 18 and 20 are respective upright sections 26 and 28 which support a pair of pressure sensing housing units denoted by the arrows S1 and S2.

Solidly secured to the front section 2 of the retainer body is a dental clamp 30 provided with a pair of arcuate arms 31 and 32. These arms 31 and 32 are shaped to fit inside the mouth of the patient P and are further formed at their inner sides with dental indentations designed to complement and fit snugly around the teeth of the patient. The arcuate arms 31 and 32 are tightly clamped against the patient's teeth by means of an adjustment screw 33.

It will be observed that the adjustable U-shaped retaining structure functions to locate the two pressure sensing housing units S1 and S2 at either side of the head of the patient when the dental clamp 30 is fastened. By slidably adjusting the end sections 4 and 6, a desired lateral spacing of the housing units relative to respective sides of the patient's head may be obtained. Similarly by slidably adjusting the side extensions 18 and 20, the housing units may be moved backwards or forwards to further locate these housing units in desired positions of adjustment. These adjustments of the retaining body, together with a suitably chosen height of the upright sections 26 and 28, provide for arranging the housing units in specially oriented relationship to the tempero mandibular joints such that the housing units lie in substantially centered relationship with respect to the horizontal axis of hinging H of the rounded ends of the condyles of the mandibular joints. This axis of hinging H is more clearly indicated in FIGS. 6—9, and as shown therein, passes through the rounded ends of the condyles and also the maxilla cavities in which the condyles are received.

Figure 4:
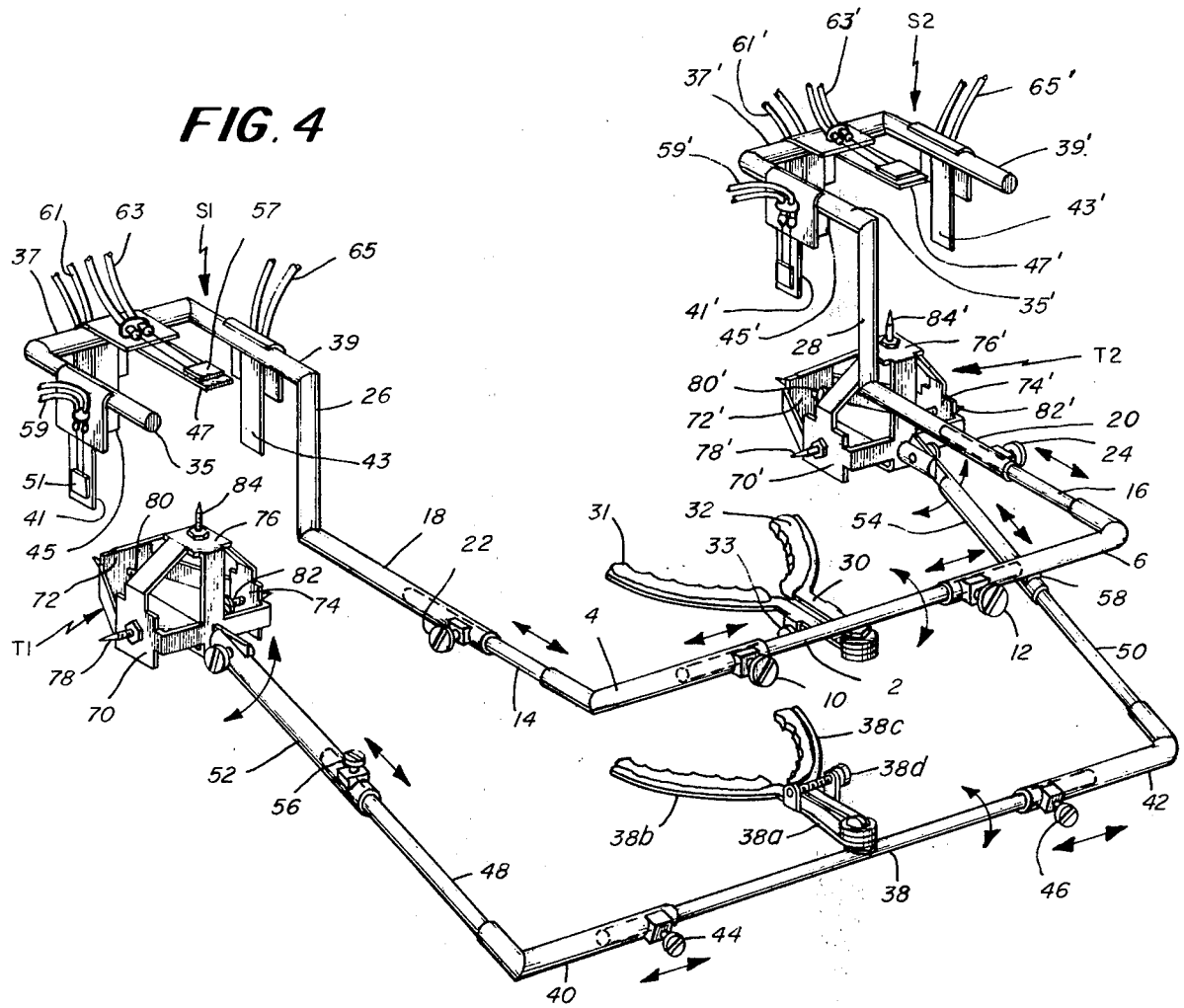
FIG. 4 is a perspective view further illustrating the sensing and pressure responsive actuator units and also showing clamping means for attaching the frame structures to the jaws of a patient.

The two pressure sensing housing units S1 and S2 are more clearly shown in FIG. 4, and as illustrated therein, the unit S1 is made up of right angularly disposed housing arms 35, 37 and 39. Yieldably supported on housing 35 is a flexible sensing element 41 occurring in a vertical plane extending substantially at right angles to the axis of hinging H. A second sensing element 43 is yieldably suspended from housing arm 39 in a plane parallel with the plane of the sensing element 41. A third sensing element 45 is yieldably suspended from the housing arm 37 in a vertical plane occurring at right angles to the said vertical planes of sensing elements 41 and 43. A fourth sensing element 47 is yieldably supported on housing arm 37 and disposed in a horizontal plane extending at right angles to the plane of sensing elements 41, 43 and 45.

Attached to each of the sensing elements are strain gauge members as 51, 53, 55 and 57 connected by conductor means 59, 61, 63 and 65 to Wheatstone Bridge and recording means R diagrammatically shown in FIG. 1 and being of conventional form.

Similar, but primed numerals denote corresponding parts of the pressure sensing housing unit S2, including sensing elements, strain gauges and conductor means.

As is further illustrated in FIGS. 1 and 4, the lower frame structure of the recording system of the invention is made up of a front section 38 on which are slidably disposed end sections 40 and 42 adapted to be secured by set screws as 44 and 46.

Mounted on this front section 38 is a dental clamp 38a having arcuate arms 38b and 38c which are formed with dental indentations and which are adapted to be solidly secured against the mandible teeth of the patient P by a set screw 38d.

The end sections 40 and 42 have right angularly shaped extremities in which are slidably received side sections 48 and 50, in turn provided with slidably disposed extension sections 52 and 54, adjustably secured by set screws 56 and 58. Adjustably secured at the outer extremities of the sections 52 and 54 is a pair of pressure transmitting actuator units T1 and T2, normally arranged to lie in nested relationship with regard to respective housing units S1 and S2.

Figure 3:
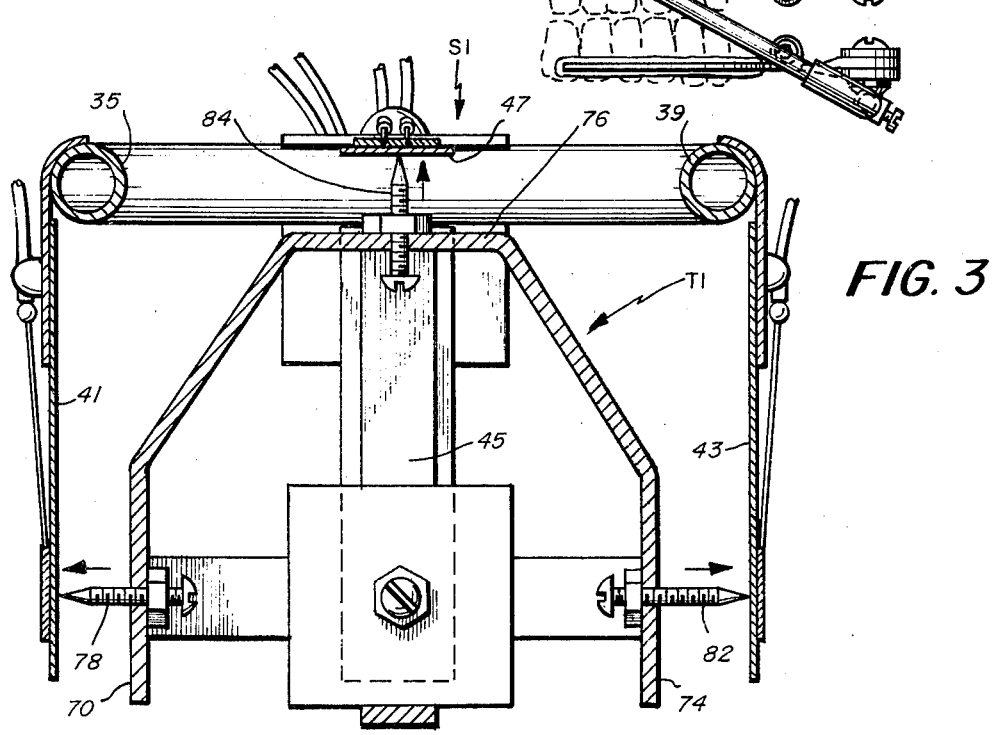
FIG. 3 is a cross section taken on line 3—3 of FIG. 2.

Included in the actuator unit T1 is a hollow contact body formed with contact retainer sides 70, 72, 74 and 76 which may be connected together, for example, by joining strips of material as shown. Transversely mounted through the retainer sides 70, 72, 74 and 76 are respective contact elements 78, 80, 82, and 84. In one preferred form the contact elements 78, 80, 82 and 84 may consist in screw members which may be threaded into desired outwardly projecting positions so as to lightly engage against respective sensing elements 41, 43, 45, and 47, as suggested in FIGS. 1 and 3. Similar but primed numerals denote corresponding parts of the actuator unit T2.

In operation, the apparatus described is attached to the patient P as shown in FIG. 1 and the contact elements of the two actuator units T1 and T2 are adjusted to lightly engage with respective sensing elements of the housing units S1 and S2. Strain gauges supported on these sensing elements are connected to Wheatstone Bridge means and recording apparatus generally denoted by the arrow R, as shown at the lefthand side of FIG. 1. The jaw and teeth of the patient are then worked moving the contact elements against the sensing elements and producing a series of displacement forces which are transmitted to the strain gauges, each of which is connected to a Wheatstone Bridge and subsequently to a paper recorder of conventional form. There is thus provided visual readings indicated in chart form as suggested in FIG. 1.

Figure 5:
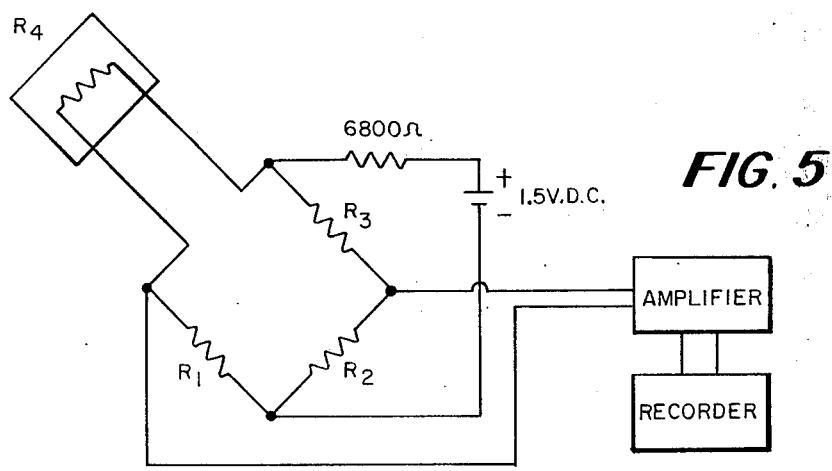
FIG. 5 is a diagrammatic view illustrating an electrical recording system.

In FIG. 5, one suitable form of amplifying and recording circuitry is shown. Also, in one desirable operation, eight channels recorded condyle movements as suggested in the chart of FIG. 1. An additional channel was utilized for recording the amount of force applied where the mandible is guided. For this purpose, chin cap 90 is applied to the patient P, as shown in FIG. 1 and connected by conductor elements 92 to the recording apparatus R.

It is pointed out that in working the jaws and teeth, displacement forces are induced which act in at least three dimensions so that all of the strain guage members are actuated and will produce signals of a significant nature. It is also pointed out that these signals are generated along the hinging axis of the mandibular condyles and respective maxillary cavities so that a desirable reference is obtained and specific relationship of the mandibular condyles with respect to the maxillary cavities is detected and observed for use in dental procedures.

In FIG. 10 there is illustrated a modified form of the recording system of the invention in which the use of strain gauges is omitted. As shown in FIG. 10, pressure sensing housing means may consist in a pair of housing units, corresponding in general to the sensing housing units S1 and S2 earlier described. It will be understood that the single housing unit shown in FIG. 10 is intended to be illustrative of a pair of such members.

As noted in FIG. 10, right angularly disposed arms 100, 102 and 104 are joined together and supported on an upright frame section 106, in turn, received on an adjustable frame structure 108, corresponding to the frame structures described with reference to housing units S1 and S2. A sensing element 110 is yieldably suspended from arm 100; also a sensing element 112 is yieldably suspended from arm 102; a sensing element 114 is suspended from arm 104; and a horizontally located sensing element 116 is also supported on arm 102.

Secured to the arms 100, 102 and 104 in spaced relation to the sensing elements 110, 112, 114, and 116, are respective bracket members 118, 120, 122 and 124. Supported through extremities of the bracket members 118, 120, 122 and 124 are micrometer members 126, 128, 130 and 132 which have respective sensing points as 126a, 130a and 132a located in contact with respective sensing elements as shown.

With a pair of sensing housings such as the one illustrated in FIG. 10, it will be understood that a pair of pressure transmitting actuator devices will be employed having the same construction and method of functioning as has been described with reference to the pressure transmitting actuator means of FIGS. 1 to 5, inclusive.

In operation, activation of the sensing elements 110, 112, 114 and 116 will produce displacement of the respective micrometers 126, 128, 130 and 132. If, for example, micrometers with an accuracy of 1/100 mm. are utilized, recordings which are accurate within 1/100 mm. can be made. For each metal strip, a micrometer and a separate recording channel is utilized. It is pointed out that by carrying out the method of the invention with direct readings, the use of Wheatstone Bridges and a paper recording apparatus is eliminated.

An important factor to be taken into consideration by a dentist involves not only postural position of condyles of a patient, but also compressiblity of the manibular joints. This is due to the specific manner in which the rounded end of a condyle is received and supported in a maxillary cavity of a manibular joint. FIGS. 6 through 9 illustrate more clearly the relationship of the mandibular joint components as well as the location of the common transverse axis of hinging of the mandibular joints.

Figure 6:
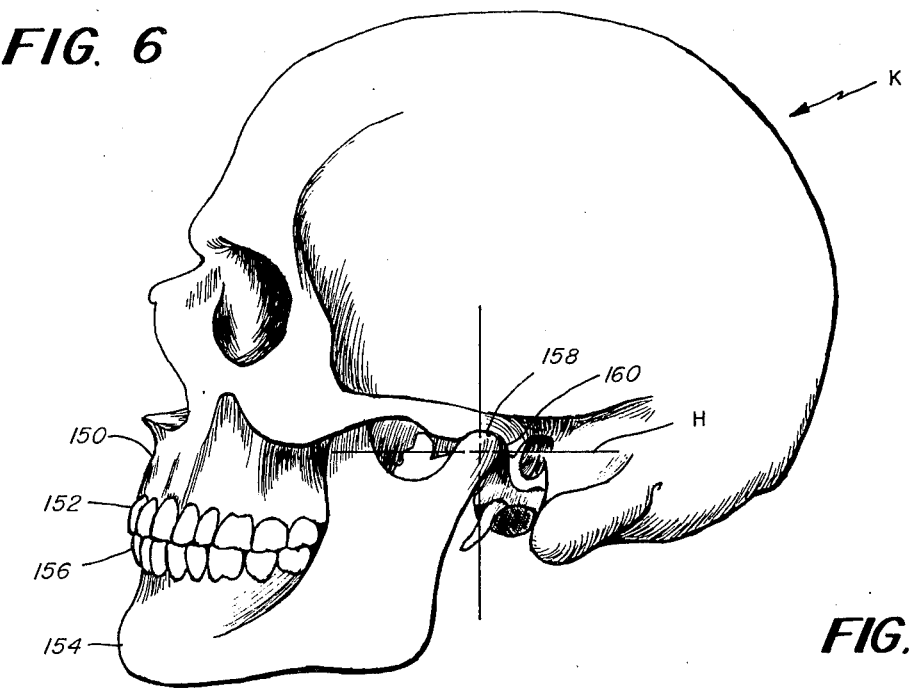
FIG. 6 is a diagrammatic view illustrating in side elevation a human skull and showing a mandibular joint through which an axis of hinging is indicated.
Figure 7:
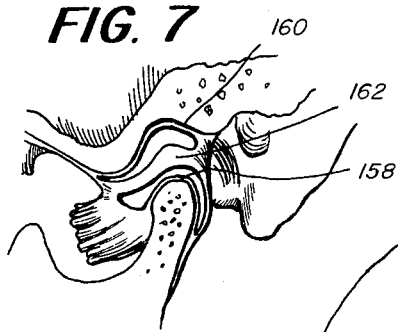
FIG. 7 is a detail fragmentary view of the tempero mandibular joint of FIG. 6 shown on a somewhat larger scale and indicating more clearly the formation of the maxillary cavity, the rounded extremity of the condyle, and a layer of tissue which occurs therebetween.
Figure 8:
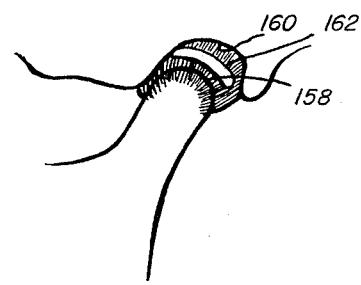
FIG. 8 is another detail fragmentary view of the condyle and maxillary cavity with the layer of tissue shown on a larger scale.
Figure 9:
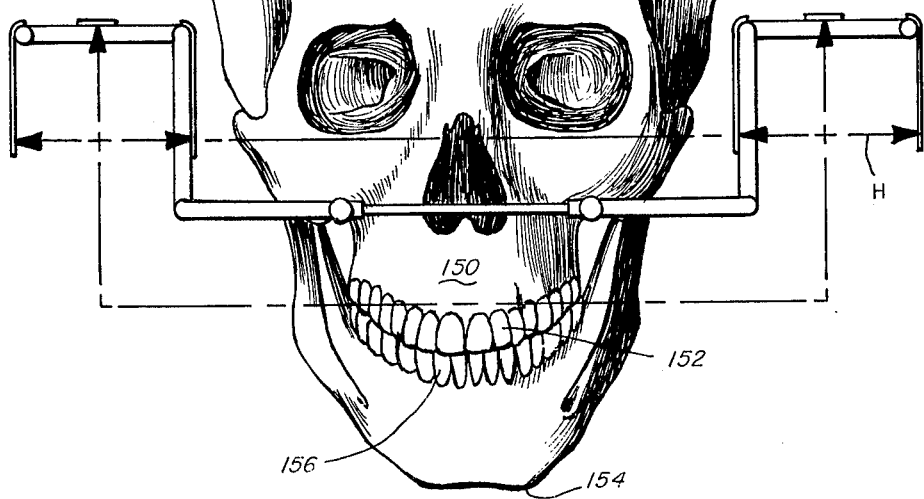
FIG. 9 is another diagrammatic view of a human skull illustrating maxillary teeth and mandibular teeth in a position of occlusion and further showing diagrammatically the common axis of hinging of the mandibular joints.

As shown in FIG. 6, a human skull, generally denoted by arrow K, includes the maxilla 150, maxillary teeth 152, mandible 154 and mandibular teeth 156. Forming a part of the mandible 154 is a condyle 158 having a rounded end portion which is received in a maxillary cavity 160. As is shown more clearly in FIGS. 7 and 8, the maxillary cavity 160 is of a somewhat enlarged shape such that the rounded end of the condyle 158 is free to more in some degree in all directions and is further cushioned against a layer of tissue 162 which is of a compressible nature. It is pointed out that the method and apparatus of the invention can be employed by a dentist to study variations in tissue compressibility of any given patient, as well as mandibular movements.

I claim:

1. Apparatus for recording condylar movements of the mandible joints of a patient when the jaws and teeth are worked, said apparatus including a pair of pressure sensing housing units having sensing elements yieldably supported therein, an upper stationary U-shaped frame structure for supporting the housing units at either side of the head of the patient along a common axis of hinging of the mandible joints, means for securing the U-shaped frame structure to the maxillary teeth of the patient, a pair of pressure transmitting actuator units having contact elements adjustably supported therein; a lower U-shaped frame structure for supporting the actuator units in nested relationship in the housing units and lightly engaging the said contact elements with respective sensing elements of the housing units, means for securing the lower frame structure to the mandibular teeth of the patient, and means for recording displacement of the sensing elements by forces transmitted through the actuator contacts in response to condylar movements of the mandible.

2. The invention of claim 1 in which the yieldably supported sensing elements are arranged to lie in a plurality of right angularly disposed planes and the contact elements of the actuator units are operable in response to condylar movements to actuate the sensing elements in any one of said planes.

3. The invention of claim 1 in which each of the sensing elements are provided with strain gauge members attached thereto and electrical means connected to the strain gauge members for recording displacement of the strain gauge members.

4. The invention of claim 1 in which each of the sensing elements is in engagement with micrometer members having pointers responsive to displacement of the sensing elements by respective contact elements.

* * * * *